United States Patent [19]

Fukushima et al.

[11] Patent Number: 4,774,259

[45] Date of Patent: Sep. 27, 1988

[54] PHENYLALANINE DERIVATIVES AND USES THEREOF

[75] Inventors: Koji Fukushima, Tama; Yoshiko Seto, Funabashi; Kazuhiro Kawada, Yokkaichi; Koji Toi; Izumi Kumashiro, both of Kawasaki, all of Japan

[73] Assignee: Ajinomoto Co., Inc., Tokyo, Japan

[21] Appl. No.: 125,572

[22] Filed: Nov. 25, 1987

Related U.S. Application Data

[63] Continuation-in-part of Ser. No. 901,364, Aug. 28, 1986, Pat. No. 4,714,713.

[30] Foreign Application Priority Data

Sep. 2, 1985 [JP] Japan .................................. 60-193565

[51] Int. Cl.$^4$ .......................................... A61K 31/195
[52] U.S. Cl. .................................... 514/563; 562/449
[58] Field of Search ......................... 514/563; 560/449

[56] References Cited

FOREIGN PATENT DOCUMENTS 59-190926  6/1984  Japan .................................. 562/443

*Primary Examiner*—James H. Reamer
*Attorney, Agent, or Firm*—Oblon, Fisher, Spivak, McClelland & Maier

[57] ABSTRACT

The invention provides a phenylalanine derivative having the structural formula:

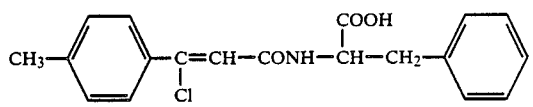

and salts thereof. The derivatives and salts are useful for promoting the absorption of medicaments such as insulin.

3 Claims, No Drawings

PHENYLALANINE DERIVATIVES AND USES THEREOF

This is a continuation-in-part of application Ser. No. 06/901,364, filed Aug. 28, 1986 now U.S. Pat. No. 4,714,713.

BACKGROUND OF THE INVENTION

1. Field of the Invention

The present invention relates to novel phenylalanine derivatives and also an absorption promoting agent comprising the phenylalanine derivatives or non-toxic salts thereof. These agents can be used to promote the oral absorption of medicaments such as insulin.

2. Discussion of the Background

Known absorption promoting agents include phenylalanine derivatives (JP-A-No. 190926/1984), benzoylpiperazine derivatives (JP-A-No. 5115/1984), and hydroxy benzoate derivatives (Biochimica et Biophysica Acta, 775, 269 to 271, 1984).

Medicaments of the polypeptide type, such as insulin, are administered only by injection, because they become inactive by the action of protein-destroying enzymes in the digestive fluid when administered orally, and because they cannot be absorbed through the intestinal tract because of their high molecular weight. However, administration by injection is not liked by patients, and therefore the development of absorption promoting agents having a low toxicity to humans is desired.

The inventors of the present invention have already desired an absorption promoting agent containing a phenylalanine derivative as an effective ingredient (JP-A-No. 190926/1984), and it is hoped that this agent will be clinically useful, particularly in the treatment of diabetes using insulin, which requires a continuous administation over a long period of time and in the case of which low dosages thereof and highly non-toxic absorption promoting agents therefor are desired.

The inventors of the present invention have studied to solve the problems as described above, and have thereby completed the present invention.

Thus, the present invention relates to the novel compound N-($\beta$-chloro-4-methylcinnamoyl)phenylalanine, which is represented by the following structural formula:

and to salts thereof. The present invention also relates to an absorption promoting agent comprising at least one such phenylalanine derivative or salt as an ingredient. The phenylalanine derivative may be in L-form, D-form or DL-form.

Previously, in U.S. Ser. No. 901,364, filed Aug. 28, 1986, Applicants have disclosed and claimed a related compound, N-($\alpha$-fluoro-4-methylcinnamoyl)phenylalanine, which is also capable of promoting absorption of medicaments such as insulin.

The pharmaceutically acceptable salts of the phenylalanine derivatives disclosed herein are inorganic salts (for example sodium, potassium, calcium or aluminium salts) or organic salts (for example, ammonium, N-acetyl-glucosamine, arginine or lysine salts).

The derivatives or salts can be administered orally or parenterally (for example, through the rectum) for achieving or promoting the absorption of medically active substances. For example, in the case of insulin, as absorption promoting effect can be attained by oral or rectal administration.

N-(4-methylcinnamoyl)-L-phenylalanine and N-($\alpha$-fluorocinnamoyl)-L-phenylalanine are disclosed in the above mentioned JP-A-No. 190926/1984. As a result of tests upon the absorption promoting effects and the safety of the compounds of the present invention, it has been found that the compounds of the present invention are better than the above two compounds. Thus, in smaller administration dosages, the compounds of the present invention have remarkable absorption promoting effects, and have higher values of oral median lethal dose ($LD_{50}$).

The absorption promoting agents of the present invention are preferably used in an amount of from 0.1 to 2,000 mg, more preferably 0.2 to 500 mg, per 25 units of the medicament, for example, insulin. The absorption promoting agent may be administered in composition form with the medicament. Thus, the derivatives or salts can be formulated into preparations such as tablets, capsules elixirs, solutions, suspensions, etc.

The N-($\beta$-chloro-4-methylcinnamoyl) phenylalanine of the present invention or the salt thereof, and the medicament such as insulin, can be administered to a patient necessitating treatment in a dosage range of, for example, 0.1 to 1,000 mg, generally several times a day, that is, in a total daily dosage of 0.2 to 2,000 mg. The dosage varies according to the seriousness of the disease, the body weight of the patient, and other factors known by those skilled in the art. The drug and absorption promoting agent may be formulated into a pharmaceutical composition as set forth below. About 0.2 to 500 mg of the phenylalanine derivative or salt and the medicament such as insulin are blended into unit dosage forms generally acknowledged or required for pharmaceutical practice, together with pharmaceutically acceptable vehicles, carriers, excipients, binders, antiseptics, stabilizers, flavorings, and so forth. The amount of each active substance in these compositions or preparations is adjusted in such a way as to give an appropriate dosage of the prescribed range.

Specific materials which can be incorporated into tablets, capsules, and so forth are as follows: binders such as tragacanth, gum arabic, cornstarch and gelatin; excipients such as microcrystalline cellulose; swelling agents such as cornstarch, pregellatinized starch, and arginic acid; lubricants such as magnesium stearate; sweeteners such as sucrose, lactose and saccharin; and flavorings such as peppermint, oil from Gaultheria adenothrix Maxim, and cherry.

Various other materials can be present as a coating material or in order to vary the physical state of the unit dosage forms. For example, tablets can be coated with shellac and/or sugar. Syrups or elixirs can contain active compounds, sucrose as a sweetener, methylparaben as a cherry flavoring and propylparaben as an orange flavoring.

Particularly in the case of insulin, an enteric coating may be used. For example, aqueous hydroxyphenylmethylcellulose solution (8%) as a precoating agent for forming an undercoat and aqueous hydroxypropylmethylcellulose phthalate solution (10%) or aqueous polyacetyne solution (3%) as coating agents may be used. When the unit dosage form of the preparation is a capsule, a liquid carrier such as a fatty oil can further be incorporated therein.

Aseptic compositions can be formulated according dosage forms, in which practice an active substance is dissolved or suspended in a vehicle such as water.

A buffer, antiseptic, or an antioxidant can further be incorporated as occasion demands.

The invention will now be illustrated by the following Examples. The Examples include those previously dislosed for N-(α-fluoro-4-methylcinnamoyl) -phenylalanine.

EXAMPLE 1 Production of N-(α-fluoro-4-methylcinnamoyl) -L-phenylalanine

Thionyl chloride (100 ml) was added to α-fluoro-4-methylcinnamic acid (12.5 g, 0.069 mole), and the mixture was stirred at 90° C. for 3 hours. The thionyl chloride was distilled off under reduced pressure, and the residue was dried and dissolved in acetone (80 ml).

L-phenylalanine (13.2 g, 0.080 mole) and 6N NaOH (43 ml, 0.086 mole) were dissolced in a solvent prepared by mixing water (77 ml) with acetone (240 ml). To the mixture, while cooling to less than 10° C. the acetone solution of α-fluoro-4-methyl cinnamic acid chloride prepared as above and 2N NaOH (38 ml, 0.076 mole) were alternately added over 20 minutes. Next, the mixture was stirred at normal temperature for 30 minutes, and the reaction solution was made acidic by the addition of 2N HCl. Then, water (200 ml) was gradually added thereto. The thus precipitated crystals were recovered by filtration and dried to give crude crystals (16.7 g). The crude crystals were recrystallized from a mixture of methanol and water to obtain N-(α-fluoro-4-methylcinnamoyl)-L-phenylalanine (yield 15.5 g) in the form of white needle-like crystals having a melting point of 163° to 163.5° C.

Elementary analysis: Found: C,69.71%; H,5.54%; N, 4.28%; F 5.80%. Calc. as $C_{19}H_{18}NO_3F$: C,69.30%; H, 5.35%; N,4.26%; F 5.45%.

Optical rotation: $[\alpha]^{25}_D = -51.2°$ (C=0.5, Methanol)

IR spectrum: $\nu^{KBr}_{max}$=3380, 3040, 1740, 1715, 1650 cm$^{-1}$

NMR spectrum: δ CDCl$_3$ 8.50, 7.32, 7.13, 6.80, 6.67, 4.93, 3.20, 2.30

EXAMPLE 2 Production of N-(α-fluoro-4-methylcinnamoyl)-D-phenylalanine

Example 1 was repeated, using D-phenylalanine in place of L-phenylalanine to obtain N-(α-fluoro-4-methylcinnamoyl) -D-phenylalanine (15.3 g) in the form of white needle-like crystals having a melting point of 163° to 163.5° C.

Elementary analysis: Found: C,69.71%; H,5.54%; N,4.28%; F,5.80%. Calc. as $C_{19}H_{18}NO_3F$: C,69.53%; H,5.51%; N,4.30%; F,5.37%.

Optical rotation: $[\alpha]^{25}_D = +50.6°$ (C=0.5, Methanol)

IR spectrum: $\nu^{KBr}_{max}$ =3380, 3050, 1740, 1715, 1650 cm$^{-1}$

NMR spectrum: δCDCl$_3$ 9.07, 7.37, 7.13, 6.87, 6.70, 4.93, 3.20, 2.30

EXAMPLE 3

Absorption Promoting Tests

A test for the promotion of the absorption of insulin was carried out upon the above-described absorption promoters and upon two known absorption promoting agents. Thus, insulin in a prescribed dose (23.3 unit/mg) and the absorption promoter, as given in the Table below, were dissolved or suspended in a 0.05M phosphate buffer. Then groups of five female ICR-CDI mice, 6 to 7 weeks old, which had not been fed for 18 hours, were orally administered with the predetermined buffer solution (0.5 ml). A predetermined time later, the blood glucose value of each group of mice was determined. The results are given in the Table.

The degree of the decrease in the blood glucose value in the case of N-(α-fluoro cinnamoyl)-L-phenylalanine and in the case of N-(4-methylcinnamoyl)-L-phenylalanine, the known absorption promoting agents, as compared with a control group, was small. On the other hand, the N-(α-fluoro-4-methyl cinnamoyl)-L-phenylalanine and N-(α-fluoro-4-methylcinnamoyl)-D-phenylalanine had an excellent effect in decreasing the blood glucose value.

EXAMPLE 4

Toxicity Tests

Predetermined amounts of the absorption promoters listed in the Table were each suspended in 0.5% CMC sodium salt solution. Groups of ten male ICR mice, 4 weeks old, were orally administered with the suspension. Two weeks thereafter, the LD$_{50}$ values were determined. The results are given in the Table.

As is clear from the Table, N-(α-fluoro-4-methylcinnamoyl) -L-phenylalanine and N-(α-fluoro-4-methylcinnamoyl) -D-phenylalanine have an excellent LD$_{50}$ value as compared with known absorption promoting agents.

In view of the above results, it can be seen that N-(α-fluoro-4-methylcinnamoyl)-L-phenylalanine and N-(α-fluoro-4-methylcinnamoyl)-D-phenylalanine are much better and more useful as absorption promoters for pharmaceutically active substances, particularly insulin, in terms of both their effect and safety.

TABLE

| | | Conditions of Test | | | | |
|---|---|---|---|---|---|---|
| | Samples | Amounts of Insulin (unit/kg) | Amounts of Insulin (mg/kg) | Time (minutes) | Blood Glucose (mg/dl) | LD$_{50}$ (g/kg) |
| | Control | 50 | — | 30 | 82.4 ± 8.1 | — |
| known compounds | N—(a-fluorocinnamoyl) L-phenylalanine | " | 150 | " | 80.6 ± 5.5 | 0.5 f 1.0 |
| | N—(4-mehylcinnamoyl) L-phenylalanine | " | " | " | 78.0 ± 7.8 | 1.0 f 2.0 |
| | N—(a-fluoro-4-methyl-cinnamoyl)-L-phenyl-alanine | " | " | " | 55.8 ± 5.3 | 3.0 f 4.0 |
| | N—(a-fluoro-4-methyl)-cinnamoyl)-D-phenyl- | " | " | " | 53.0 ± 5.7 | 3.0 f 4.0 |

TABLE-continued

| | Conditions of Test | | | | |
|---|---|---|---|---|---|
| Samples | Amounts of Insulin (unit/kg) | Amounts of Insulin (mg/kg) | Time (minutes) | Blood Glucose (mg/dl) | LD$_{50}$ (g/kg) |
| alanine | | | | | |

EXAMPLE 5

Production of N-($\beta$-chloro-4-methylcinnamoyl)-L-phenylalanine

Thionyl chloride (40 ml) was added to $\beta$-chloro-4-methylcinnamic acid (6.0 g, 30.5 mmole), prepared by the method of A-H.A Youssel et. al. (J. Org. Chem., 40, 3227, 1975), and the mixture was stirred at 90° C. for 3 hours. The excess thionyl chloride was distilled off under reduced pressure, and the residue was dried and dissolved in acetone (50 ml).

L-Phenylalanine (5.8 g, 35.1 mmole) was dissolved in 2N NaOH (19.1 ml, 38.2 mmole). Then water (40 ml) and acetone (80 ml) were added. To the mixture, $\beta$-chloro-4-methylcinnamic acid chloride prepared as above in 50 ml of acetone and 2N NaOH (16.8 ml, 33.6 mmole) were alternately added over 20 minutes while keeping the reaction temperature below 10° C.

Next, the mixture was stirred at room temperature for 30 minutes. Then the mixture was acidified with 2N HCl and diluted with water (200 ml).

The precipitated crystals obtained by filtration were dissolved in ethyl acetate (200 ml) and washed with water (150 ml) and brine (100 ml). The organic layer was dried over anhydrous magnesium sulfate and the solvent was distilled off. The residual products were recrystallized from ethyl acetate and n-hexane to produce N-($\beta$-chloro-4-methylcinnamoyl)-L-phenylalanine (yield 7.0 g) in the form of white crystals having a melting point of 168.5° to 169.5° C.

Elementary analysis: Found: C,66.41%; H,5.20%; N,4.02%; Cl,10.48%. Calc. as C$_{19}$H$_{18}$NO$_3$Cl: C,66.37%; H,5.20%; N,4.08%; Cl,10.31%.

Optical rotation: $[\alpha]_D^{25} = -14.2°$ (C 1.0, Methanol)

MS spectrum (FD-MS):
M+ = m/z 343

NMR spectrum:
$^1$H, 90 MHz
$\delta$DMSO-d6  2.32(s,3H),  2.75-3.30(m,2H), 4.40-4.70(m,1H)  6.75(s,1H),  7.13(s,5H), 7.00-7.55(m,4H) 8.16(d,1H), 11.40(br.s,1H)

EXAMPLE 6

Production of N-($\beta$-chloro-4-methylcinnamoyl)-D-phenylalanine

The method of example 5 was repeated, using D-phenylalanine in place of L-phenylalanine to obtain N-($\beta$-chloro-4-methylcinnamoyl)-D-phenylalanine (6.50 g) in the form of white crystals having a melting point of 168.5° to 169.5° C.

Elementary analysis: Found: C,66.58%; H,5.47%; N,4.09%; Cl; 10.36%. Calc as C$_{19}$H$_{18}$NO$_3$Cl: C,66.37%; H,5.28%; N,4.08%; Cl, 10.31%.

Optical rotation: $[\alpha]^{25}{}_D = +14.3$ (C=1.0, Methanol)
MS spectrum (FD-MS): M+ = m/z 343
NMR spectrum:
$^1$H 90 MHz
$\delta$  DMSO-d6  2.32(s,3H),  2.75-3.30(m,2H), 4.40-4.70(m,1H)  6.75(s,1H),  7.00-7.55(m,9H), 8.16(d,1H)

EXAMPLE 7

Absorption Promoting Test

A test for the absorption of insulin was carried out with absorption promoters of the present invention. Thus, insulin (0.5 unit/10 g weight) and the absorption promoter (3 mg/10 g weight) were suspended in a 0.05M phosphate buffer. Then the group of five female ICR-CD1 mice, 5 to 7 weeks old, which were fasted for 18 hours, were orally administered with the prepared suspension.

The blood glucose value and the immunoreactive insulin level of each group of mice were determined at the fixed time.

The percent decrease in blood glucose and the degree of increase of blood insulin as compared with a phosphate buffer control group were shown in Table 2.

As is clear from the Table 2, N-($\beta$-chloro-4-methylcinnamoyl)-L-phenylalanine and N-($\beta$-chloro-4-methylcinnamoyl)-D-phenylalanine of the present invention have an excellent effect on decreasing the blood glucose value and increasing the blood insulin level.

EXAMPLE 8

Toxicity Tests

Predetermined amounts of the absorption promoters listed in Table 2 were each suspended in 0.5% CMC sodium salt solution. Groups of ten male ICR mice, 4 weeks old, were orally administered with the suspension. Two weeks thereafter, the number of survival was determined. The results are given in Table 3.

As is clear from Table 3, the N-($\beta$-chloro-4-methylcinnamoyl)-L-phenylalanine and N-($\beta$-chloro-4-methylcinnamoyl)-D-phenylalanine of the present invention have an excellent LD$_{50}$ value (73.0 g/kg) as compared with that of known absorption promoting agents.

In view of the above results, it can be seen that N-($\beta$-chloro-4-methylcinnamoyl)-L-phenylalanine and N-($\beta$-chloro-4-methylcinnamoyl)-D-phenylalanine are much better and more useful as absorption promoters for pharmaceutically active substances, particularly insulin, in terms of both their effect and safety.

TABLE 2

| | (1) Decrease in Blood Glucose (%) (2) Degree of increase of Blood Insulin time (minutes) | | |
|---|---|---|---|
| sample | 15 | 30 | 60 |
| N—($\beta$-chloro-4-methyl-cinnamoyl)-L-phenylalanine | (1) 42.1 (2) 10.5 | (1) 21.6 (2) 2.0 | 12.1 2.1 |
| N—($\beta$-chloro-4-methyl-cinnamoyl)-D-phenylalanine | (1) 35.7 (2) 2.1 | (1) 47.8 (2) 3.3 | 42.8 1.0 |

TABLE 3

| sample | Number of Survival* dose | |
| --- | --- | --- |
|  | 1.0 g/kg | 3.0 g/kg |
| N—(β-chloro-4-methyl-cinnamoyl)-L-phenylalanine | 10 | 10 |
| N—(β-chloro-4-methyl-cinnamoyl)-D-phenylalanine | 10 | 6 |

*at beginning, number = 10

What is claimed as new and desired to be secured by letters patent of the United States is:

1. A phenylalanine derivative having the structural formula:

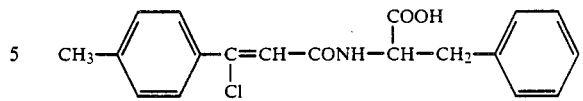

or a pharmaceutically acceptable acid addition salt thereof.

2. A pharmaceutical composition comprising a phenylalanine derivative as claimed in claim 1 and insulin.

3. A composition as claimed in claim 2, further comprising a pharmaceutically acceptable carrier or diluent.

* * * * *